US005846559A

United States Patent [19]

Hopp

[11] Patent Number: 5,846,559

[45] Date of Patent: Dec. 8, 1998

[54] SKIN PATCH FOR USE IN CONTACT IMMUNOTHERAPY

[76] Inventor: Robert B. Hopp, 969 Stevens Dr. Suite 1C, Richland, Wash. 99352

[21] Appl. No.: 717,108

[22] Filed: Sep. 20, 1996

Related U.S. Application Data

[62] Division of Ser. No. 421,449, Apr. 12, 1995, abandoned.

[51] Int. Cl.[6] .......... A61F 13/02

[52] U.S. Cl. .......... 424/448; 424/447; 424/449

[58] Field of Search .......... 424/448, 449, 424/447

[56] References Cited

U.S. PATENT DOCUMENTS

| 5,188,509 | 2/1993 | Amkraut | 424/449 |
|---|---|---|---|
| 5,273,755 | 12/1993 | Venkatrama | 424/448 |

OTHER PUBLICATIONS

Orecchia, G., et al., "Treatment of multiple relapsing warts with diphenciprone", *Dermatologica,* vol. 177 No. 4, 225–231(1988).

Claudy, A.–L., et.al., "Immunotherapy of mulitple recurring warts. II. Reassessement of the use of squaric acid dibutylester (SADBE)", *Ann.Dermatol. venereot.* (*Paris*), vol. 108, 765–767 (1981).

Sanders, Beverly B., et al., "Dinitrochlorobenzene immunotherapy of human warts", *CUTIS,* vol. 27, 389–392 (1981).

Naylor, Mark F., et al, "Contact immunotherapy of resistant warts", *Journal of the America Academy of Dermatology,* vol. 19, No. 4, Oct. 1988.

Lee, Sungnack, et al., "Therapeutic effect of dinitrochlorobenzene (DNCB) on verruca plana and verruca vulgaris", *International Journal of Dermatology* vol. 29, No. 9, Nov. 1984.

Dunagin, W.G., et al., "Dinitrochlorobenzene immunotherapy for verrucae resistant to standard treatment modalities", *Journal of the American Academy of Dermatology,* vol. 6, No. 1, Jan. 1982.

Ericksen, Knud., "Treatment of the common wart by induced allergic inflammation", *Dermatologica,* vol. 160, 161–166 (1980).

Greenburg, Joseph H., et al. "Verrucae vulgaris rejection", *Arch Dermatol,* vol. 107, 580–582, Apr. 1973.

Buckner, Dorothy, et al, "Immunotherapy of verrucae vulgares with dinitrochlorobenzene", *British Journal of Deramtology,* vol. 98, 451–455 (1978).

Lewis, Henry, "Topical immunotherapy of refractory warts", *CUTIS,* vol. 12, 863–867, Dec. 1973.

*Primary Examiner*—D. Gabrielle Phelan
*Attorney, Agent, or Firm*—Stephen R. May

[57] ABSTRACT

A skin patch is disclosed for usage in the delivery of a contactant to human skin for the purpose of treating medical conditions responsive to contact immunotherapy. The skin patch specifically induces a cell-mediated contact dermatitis in the treatment of skin disorders. Its anticipated use pertains to treatment of human papilloma virus infections, or warts. In a first embodiment, a pressure activated single chambered skin patch is topically applied and used for controlled release of contactant to human skin. In a second embodiment, a pressure activated two chambered skin patch is topically applied and used for controlled release of a contactant to human skin. Alternatively, a single chambered skin patch is topically applied and hydrated by the contacted skin for release of contactant. In addition, a flared shroud region can be provided between the containment portion of the shroud and a surrounding adhesive flange to enlarge the area treated upon release of the contactant. The contactants include dinitrochlorobenzene, diphenylcyclopropenone, squaric acid dibutyl ester, and their derivatives.

14 Claims, 5 Drawing Sheets

13
10
12
11
16
15
14
14
14

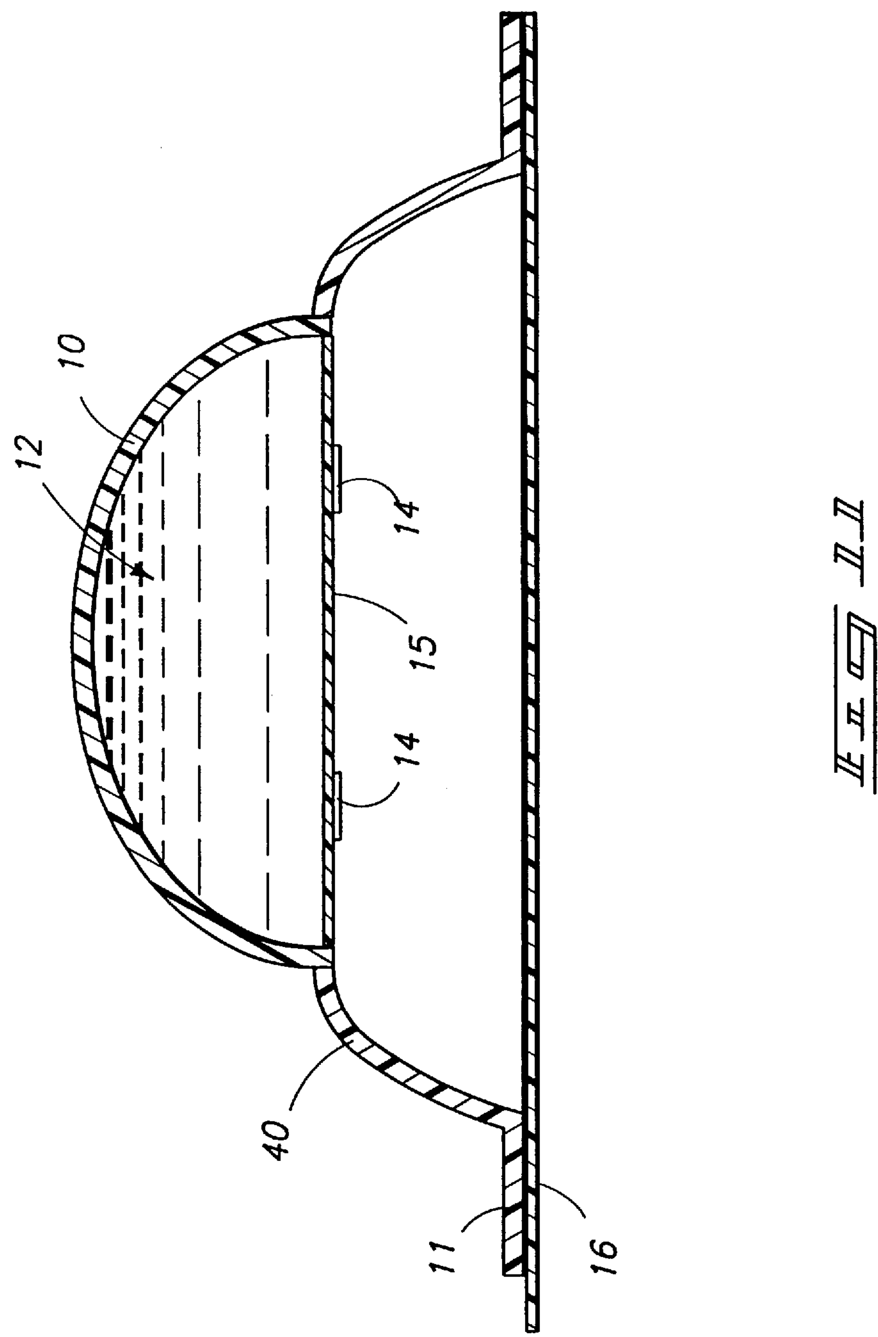
10
12
14
15
14
40
11
16

SKIN PATCH FOR USE IN CONTACT IMMUNOTHERAPY

CROSS-REFERENCE TO RELATED APPLICATIONS

This is a division of application Ser. No.: 08/421,499, filed: Apr. 12, 1995, now abandoned.

TECHNICAL FIELD

This disclosure pertains to a skin patch for delivery of an active contactant that induces a contact dermatitis for treatment of medical conditions responsive to contact immunotherapy. Examples are human papilloma viral infections (warts).

BACKGROUND OF THE INVENTION

While not limited in its specific medical application, the contactant delivery system described herein was developed as an effective means for treating human papilloma viral infections, or warts.

Human papilloma viral infections are a common infection of the outer layer of skin affecting most persons sometime during their lifetime. An incidence of 10% for children and young adults in the general population has been estimated. Although the majority of such infections are benign and self-limited, there are subtypes of papilloma virus that are considered premalignant in certain clinical settings. Many persons afflicted with warts seek treatment for these cutaneous infections, but to date most methods are painful, expensive, time consuming or ineffective. These methods include applications of liquid nitrogen, electrocautery techniques, carbon dioxide laser energy, trichloroacetic acid, podophyllin, canthridin, formaldehyde, glutaradehyde, 5-flurouracil, bleomycin, surgical procedures, and administration of interferon.

For many years human papilloma viral infections have been treated with topical agents that are applied as solutions, tinctures, creams, ointments, etc. The various agents applied in this fashion have included caustic chemicals that act through nonspecific destructive mechanisms to cause the cell death of the keratinocytes infected with the viral particles. The keratinocytes subsequently are desquamated from the skin surface. The side-effects of this non-specific form of destructive therapy can be pain, secondary infection, permanent scarring and recurrence. In a similar fashion, physical treatments for destroying the infected keratinocytes by cooling (e.g. liquid nitrogen) or heating (e.g. electrocautery, $CO_2$ laser) can likewise lead to injury of surrounding tissue and other undesired consequences.

There are numerous agents that can induce a contact dermatitis in human skin. Therapeutically, these have included dinitrochlorobenzene, diphenylcyclopropenone and squaric acid dibutyl ester. When these allergens are applied to human skin they provoke an allergic or type IV immune reaction referred to as a contact dermatitis. This reaction involves the production of a cell-mediated immunity against the applied antigen by the host. The observable reaction at the site of application of the allergen is an erythematous rash. This reaction is very specific for the allergen applied and, although itchy, is not painful and does not lead to scarring. An overview of such contact immunotherapy treatments for warts is found in a paper titled "Contact immunotherapy of resistant warts" by Naylor et al., published in *The Journal of the American Academy of Dermatology*, Vol. 19, No. 4, October, 1988 at Pages 679–683, which is hereby incorporated into this disclosure by reference.

It has been recognized that the induction of a contact dermatitis around warts can produce an immunity in the host and subsequent resolution of the human papilloma viral infection. The repeated application of any contactant to the skin induces lymphocytes to aggregate in the area of application, in this case around the wart. These immune cells, along with other cells found in the skin, are responsible for the production of anti-viral antibodies and cell-mediated immunity against the human papilloma virus. These results have previously been demonstrated to develop after successful treatment of papilloma viral infections. The immune response induced by the application of contactant to skin is thought to be responsible for the resolution of warts. It is currently felt that cell-mediated immunity plays the most important role in resolution of these infections.

The advantages of contact sensitization in the treatment of warts are ease of application, relatively low cost, safety, specificity and, most importantly, the painless nature of the treatment. However, there is presently no dosage controlled delivery system for the application of contactants to the skin. The state of the art today is to dilute the contactant in acetone and apply it with a cotton tipped applicator. The dose of contactant delivered and the application schedule has varied widely in reported studies.

BRIEF DESCRIPTION OF THE DRAWINGS

Preferred embodiments of the invention are described below with reference to the accompanying drawings, which are briefly described below.

FIG. 11 is a schematic sectional view of a fourth embodiment of the skin patch.

DETAILED DESCRIPTION OF THE PREFERRED EMBODIMENTS

Figure 1:
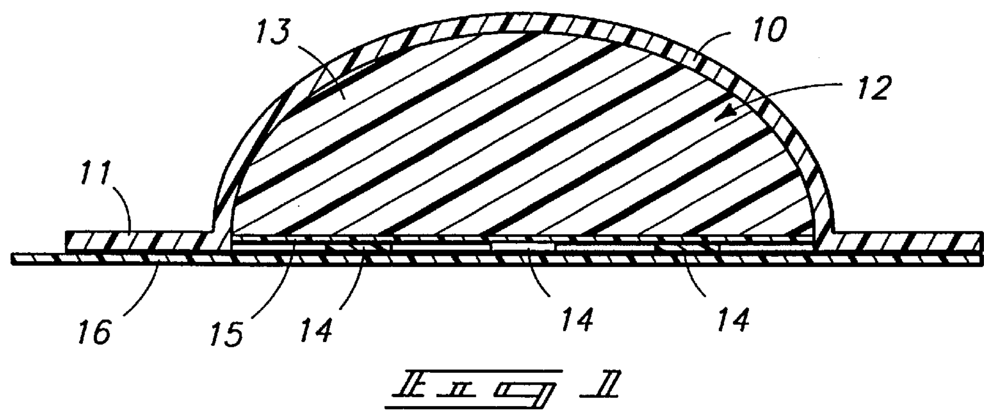
FIG. 1 is a schematic sectional view of a first embodiment of the skin patch.
Figure 2:
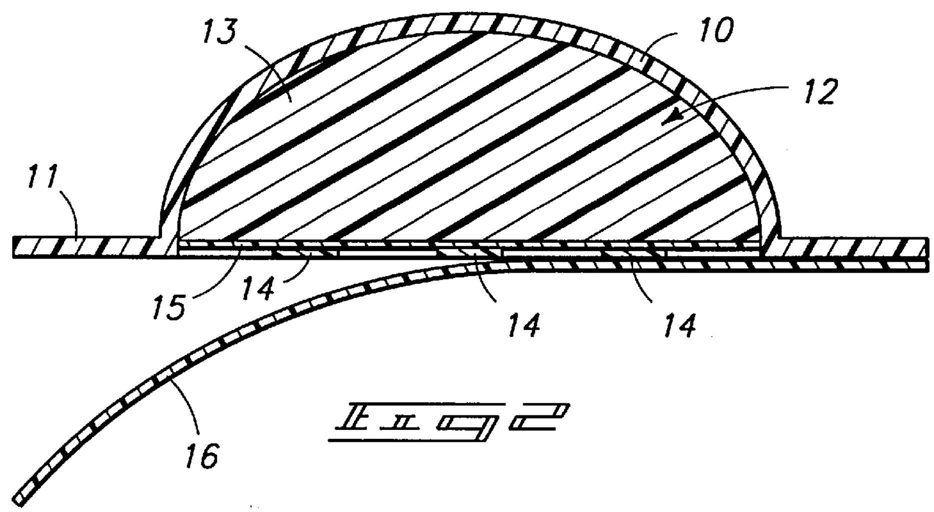
FIG. 2 is a view illustrating removal of the backing layer.
Figure 3:
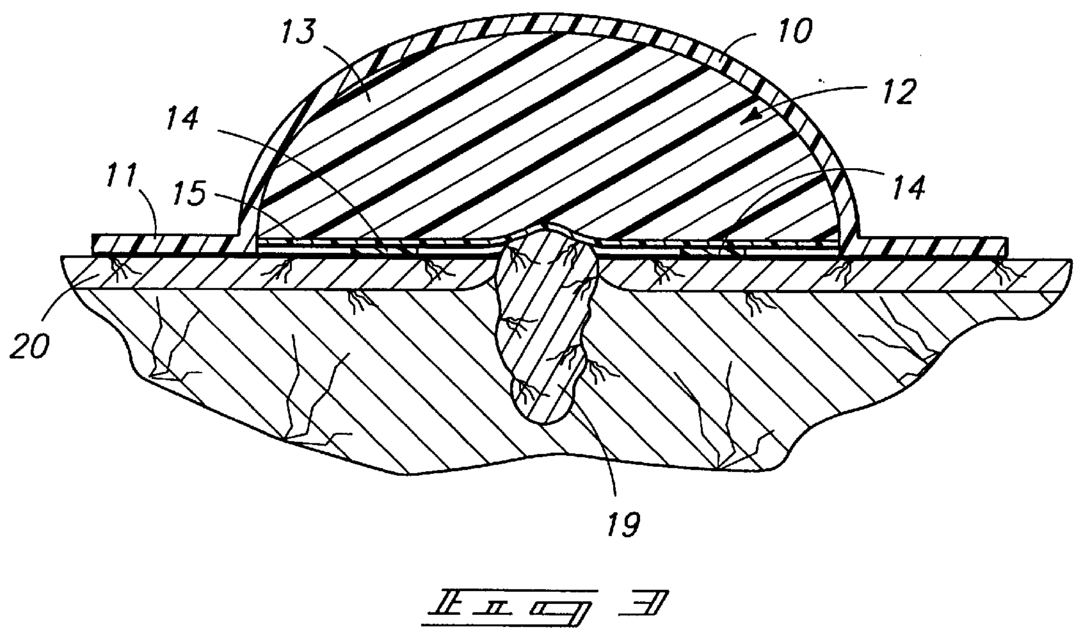
FIG. 3 is a view illustrating placement of the skin patch on a wart.
Figure 4:
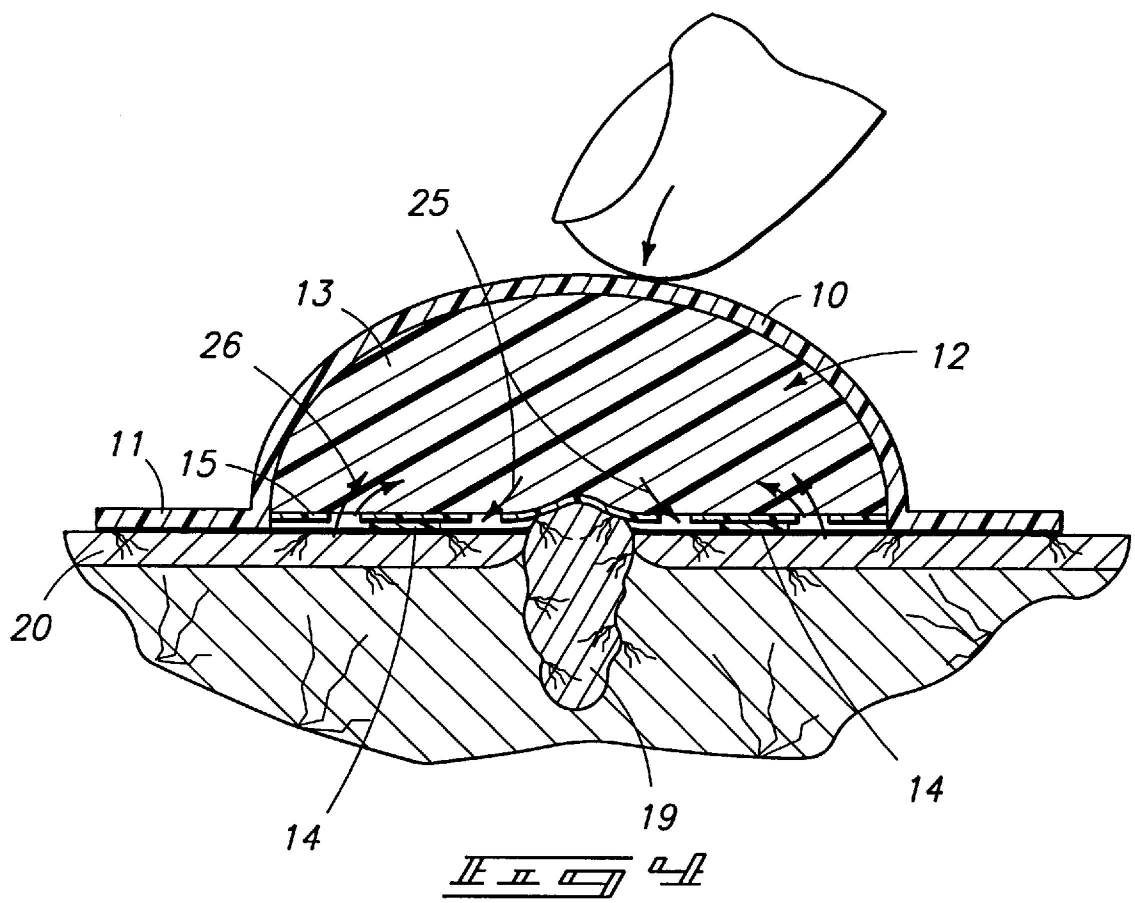
FIG. 4 is a view illustrating application of pressure and release of contactant.

This disclosure of the invention is submitted in furtherance of the constitutional purposes of the U.S. Patent Laws "to promote the progress of science and useful arts" (Article 1, Section 8).

The skin patches shown in the drawings were designed to deliver a contactant to human skin for the treatment of cutaneous disorders, specifically human papilloma viral infections (warts). They provide a simple and effective means for inducing a type IV cell mediated immune response in a patient.

Alternative therapeutic applications include treatment of other cutaneous viral infections, such as Molluscum contagiosum, Herpes simplex, and Herpes Zoster. Additionally chronic cutaneous fungal infections may be amenable to treatment, such as Dermatophyte infections and mycetoma. Skin malignancies such as basal cell carcinoma, squamous cell carcinoma and melanoma are included within other medical applications where the production of a contact dermatitis is known to enhance rejection of a tumor by the affected host. Alopecia areata, a condition producing hair loss through immune mechanisms, can also be treated.

The delivery device might also be used to enhance the function of the immune system in persons having states of immune deficiency e.g. AIDS, transplantation reactions, and hereditary immune deficiencies. The device could also be adapted to test for the level of immune function, by testing for the degree of contact sensitivity, in these same patients.

In general, the illustrated forms of the skin patch are designed for topical administration of controlled quantities of a contactant that induces a contact dermatitis for treatment of a medical condition responsive to contact immunotherapy. Each patch supplies a standardized dosage of an active liquid contactant partially enclosed within a covering shroud. Adhesive means is associated about the shroud for temporarily and releasably attaching it to the skin of a user with the active contactant juxtaposed to the skin surface. A discardable release liner is releasably bonded to the adhesive means for covering the adhesive means prior to use of the skin patch.

The active contactant is selected from the group comprised of dinitrochlorobenzene, squaric acid dibutyl ester, diphenylcyclopropenone and their derivatives.

There are several aspects about this system that are advantageous when compared to prior treatment modalities for application of these known contactants. Identified advantages of this dosage controlled delivery system include: (1) standardized dosing; (2) safety from unintended exposure to the contactant; (3) ease of use by ancillary medical personnel; (4) localization of the contactant to the treatment area; (5) stabilized storage form; (6) provision of a dye to mark the treatment area; (7) increased penetration of the contactant established by hydration and occlusion of the skin; and (8) ability to use penetration enhancers in combination with the contactant to increase the permeability of the contactant.

Most importantly, the use of a skin patch delivery system allows the application of a standardized and predetermined amount of contactant to an affected skin area. This is an advantage over previous systems, which consisted of applying liquid contactant manually by using a cotton applicator. The applied dose of the contactant is then not known. The method of application for the contactant by use of a skin patch becomes standardized and reproducible. It is no longer dependent on the individual who is applying the contactant.

Standardized dosing also permits the comparison of different dose schedules and concentrations to establish the most effective parameters needed for successfully treating papilloma viral infections. The controlled dosing that results from use of this system allows titration of the medication to the immune response by the host. It also facilitates comparison studies between different contactants based on doses and concentrations. The use of a skin patch delivery system will facilitate studies to determine optimum rates of release of contactant and to measure the exposure times that yield optimal treatment results.

Polymer gels are used today for delivery of medications topically to the skin and function also as wound dressings. Polymer gel matrices have several known advantages as drug delivery devices, including their biocompatability, ability to swell when contacted by water, and ability to control the rate of release of medication to the skin. These gels can be designed for the controlled release of medication through modification of the proportion of monomer and cross-linking used in their manufacture. Medications can be introduced into matrices through the use of organic solvents or during manufacturing of the gel. The release of medication can be controlled by adjustment of the swelling ratio on contact with water.

When used in the disclosed skin patches, polymer gel matrices can be designed to control both the concentration and release of contactant. The total dose of active ingredient available in a skin patch is dependent on the quantity of contactant added at the time of production. Control of the rate of contactant release is dependent on the percent concentration of the monomer within a gel matrix and the amount of cross-linking used in its manufacture. The rate of release of contactant from the gel matrix can be further modified by interposed membranes which limit the rate of diffusion between the contactant reservoir of the skin patch and the skin.

Safety is another feature that is enhanced by the design of this delivery system, both for the patient and health care provider. It is important to guard against accidental exposure to the active contactant on the part of persons handling and applying the delivery device. The described device will not be activated until desired treatment time. The isolation of the contactant in the gel matrix, surrounding containment shroud, impermeable adhesive layer, and peel away backing prevents unintentional exposure to the contactant. This permits safe transportation and storage.

The adhesive system surrounding the skin patch keeps the contactant confined about the intended point of application and avoids contact with non-treatment areas about the skin. The occlusive nature of the device increases the penetration of contactant into the skin and thereby increases the effectiveness of treatment.

The principal means of enhancement of penetration is through an increase in the hydration of the stratum corneum and the subsequent increase in permeability of the skin to the contactant. Permeability can be increased by providing excess solvent in the device, thereby making areas of the skin which are normally dry, more amenable to treatment. The use of a solvent which enhances skin penetration, such as butanol with squaric acid dibutyl ester, not only increases penetration of the contactant, but also prevents its degradation.

The included indicator dye provides visual confirmation of the working progress of the device. Released dye can be viewed through the transparent shroud of the device, or alternately through a window at the apex of the device, to warn both the patient and health care provider that the skin patch is active.

The indicator dye provided within the disclosed system limits the time the device needs to be on the patient and also indicates that the desired dose of contactant has been delivered. By knowing the rate of diffusion of the contactant and indicator dye through the matrix, a fixed amount of skin exposure to contactant can be calculated and determined to have occurred before the color becomes visible at the window. The visual dye system also confirms that the device has been successfully activated. It avoids treatment failure by unintentionally failing to activate the skin patch during application to the skin.

The presence of residual dye on the skin provides a continuing visual indication of the area of contact after removal of the skin patch. It also serves as a reminder to wash off any remaining excess contactant.

The use of a contactant benefits the patient by providing a non-toxic, painless means of treatment. Since many patients with warts are children, a painless therapy is desirable in obtaining patient cooperation and compliance. Surgical procedures and subsequent morbidity and scarring are avoided, as well as the anxiety that accompanies these procedures.

The development of immunity to papilloma virus infections as a result of using this device is of long term benefit. Such immunity continues after the present viral infection is successfully resolved. The prevention of reinfection generates cost savings of both time and money, making future treatments for reinfection by warts unnecessary. Additionally ancillary personnel can be trained to in the use of this device at a cost saving to the patient, obviating the need for highly trained specialists.

FIRST EMBODIMENT

The first and preferred embodiment of the skin patch is a single reservoir delivery device shown schematically in FIGS. 1–5. The illustrated skin patch includes a supply of contactant enclosed within an enclosing shroud 10.

The shroud 10 consists of a flexible shell that contours with the skin surface. It must be sufficiently flexible to accommodate bending and motion of the supporting the skin surface (generally indicated at 20). Shroud 10 must be waterproof and resistant to solvents and contactants. It is preferably transparent, or translucent. A transparent window (not shown) might be provided at the apex of the shroud 10 if desired.

As shown in FIGS. 1–4, the entire shroud 10 can be made of a clear, light transmitting material. It can be constructed as a single layer or as a laminate of two or more layers of metalized elements or composite coated elements. Examples of suitable materials for the shroud include (without limitation): ethylene vinyl acetate copolymers, polyesters, metalized polyesters, polyethylenes, polycarbonates, polyvinyl chlorides, polyvinylidene fluoride, polysulfones, or laminates of the above, such as metalized polyesters/EVA or medium density polyethylene/EVA.

In this form of the device, the adhesive coated flange 11 surrounding the shroud 10 is formed integrally with it. Alternatively the adhesive flange 11 could be formed as a separate annular element sealed about the rim of the shroud 10. Examples of suitable materials for the adhesive flange 11 include silicon rubber, cellophane, cellulose acetate, ethylcellulose, plasticized vinylacetate-vinylchloride copolymers, polyethylene terephthalate, nylon, polyethylene, polypropylene, polyvinylidenechloride, aluminum foil and sylanized polyester.

The outer surface or undersurface of the adhesive flange 11 is coated with an adhesive that assures persistence of the device on the skin. The selected adhesive must be impermeable to water, solvent and contactant. Adhesives usable about the flange include silicone adhesives, polyacrylates, isobutylene-mineral oil, tackified styrene-isoprene-styrene block copolymers, tackified ethylene vinyl acetate copolymers, contact adhesives, and polyacrylamides.

The containment chamber 12 formed within the skin patch contains an active contactant and a solvent, such as water, acetone or butanol in sufficient quantity to saturate a gel matrix 13 that serves as an inert liquid reservoir in this system. The required characteristics of the solvent are that the contactant is soluble in it, and that it is non-toxic and does not interact chemically with the contactant, indicator dye or gel matrix.

Contactants usable in the skin patch include dinitrochlorobenzene, diphenylcyclopropenone and squaric acid dibutyl ester, as well as derivatives of these compounds.

The solvent and dissolved contactant will be released to the underlying skin upon the rupture of a thin membrane 15 forming the floor of the containment chamber 12. Containment chamber 12 might also contain a preservative or auxiliary gelling agent.

In the preferred embodiment schematically shown in FIGS. 1–5, the contactant and solvent are included within a gel matrix 13 that partially or completely fills the containment chamber 12. Suitable materials for formation of a gel matrix 13 include, but are not limited to, polymeric materials, natural and synthetic rubbers, carboxymethylcellulose, mineral oil, petrolatum and adhesives. A transparent gel matrix for this purpose is polyvinylpyrrolidone.

In place of a gel matrix, the active contactant and solvent might be contained within a viscous inert liquid carrier.

The gel matrix 13 within the containment chamber 12 can contain varying concentrations of contactants from 0.001% to 30% by weight. It preferably contains a 2% concentration of contactant by weight. The selected contactant, such as squaric acid dibutyl ester, is interspersed evenly throughout the gel matrix 13. Upon contact with solvent, gel matrix 13 will release the contactant onto a juxtaposed area about the skin 20 surrounding a wart 19 that is being treated. See FIGS. 3 and 4.

More specifically, the skin patch might include a 2% solution of squaric acid dibutyl ester dispersed in a hydrogel matrix made of a polyurethane/acrylate copolymer. The preferred solvent provided within the gel matrix 13 is butanol. It should be added to the gel matrix 13 within the single contactant reservoir 12 in an amount sufficient to saturate the gel mass.

Alternative concentrations of squaric acid dibutyl ester may enhance the response to treatment in some patients or in certain areas of application. Other contactants, such as dinitrochlorobenzene and diphenylcyclopropenone could be substituted in persons who could not be sensitized to squaric acid dibutyl ester. The application of derivatives of the previously mentioned contactants can increase the penetration of the contactant or improve the quality of the immune response. This delivery system can also be modified to include additional agents that enhance penetration of the skin to the contactant, such as salicylic acid.

The indicator dye is stored in one or more small paper discs 14 on the skin contact side of a covering rupturable membrane 15, which encloses the containment chamber 12 across the open side of the shroud. The indicator dye, when contacted by solvent, will diffuse back through the gel matrix on contact with the solvent. The dye will also diffuse onto the skin, thereby marking the area of treatment. Desired characteristics of the dye are that it be capable of diffusing through the matrix, that it does not interact chemically with the contactant, that it not be toxic to human skin, and that the contactant be soluble in it. Examples of suitable dyes include gentian violet or food dyes.

Figure 5:
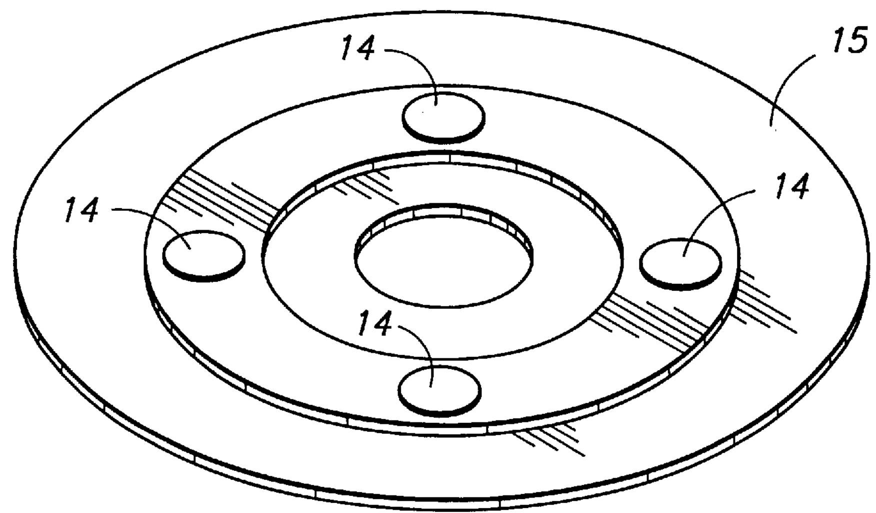
FIG. 5 is a view of an illustrative rupturable membrane.
Figure 6:
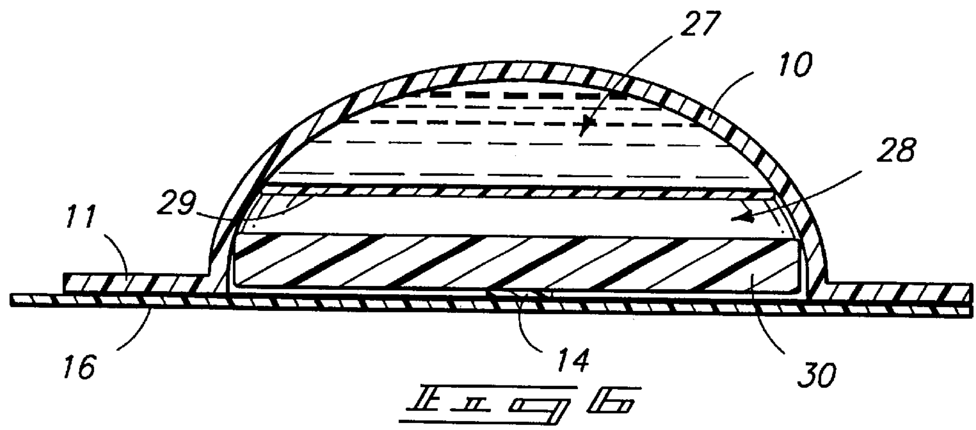
FIG. 6 is a schematic sectional view of a second embodiment of the skin patch.
Figure 7:
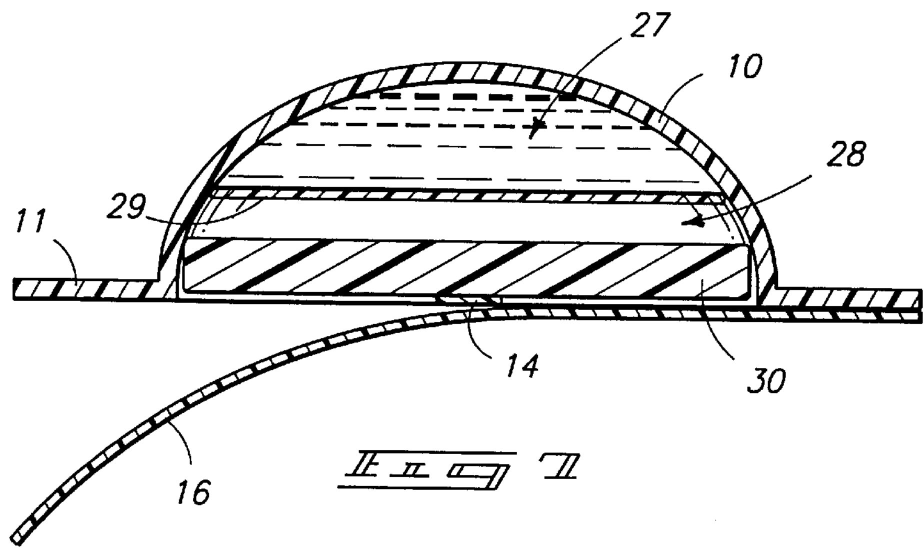
FIG. 7 is a view illustrating removal of the backing layer.
Figure 8:
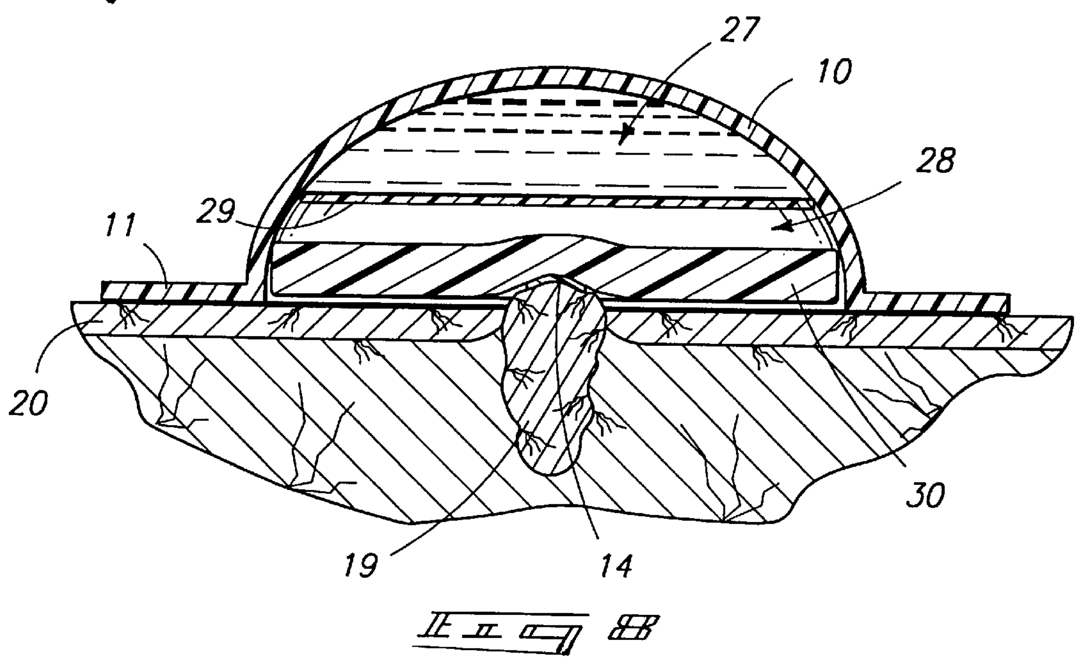
FIG. 8 is a view illustrating placement of the skin patch on a wart.
Figure 9:
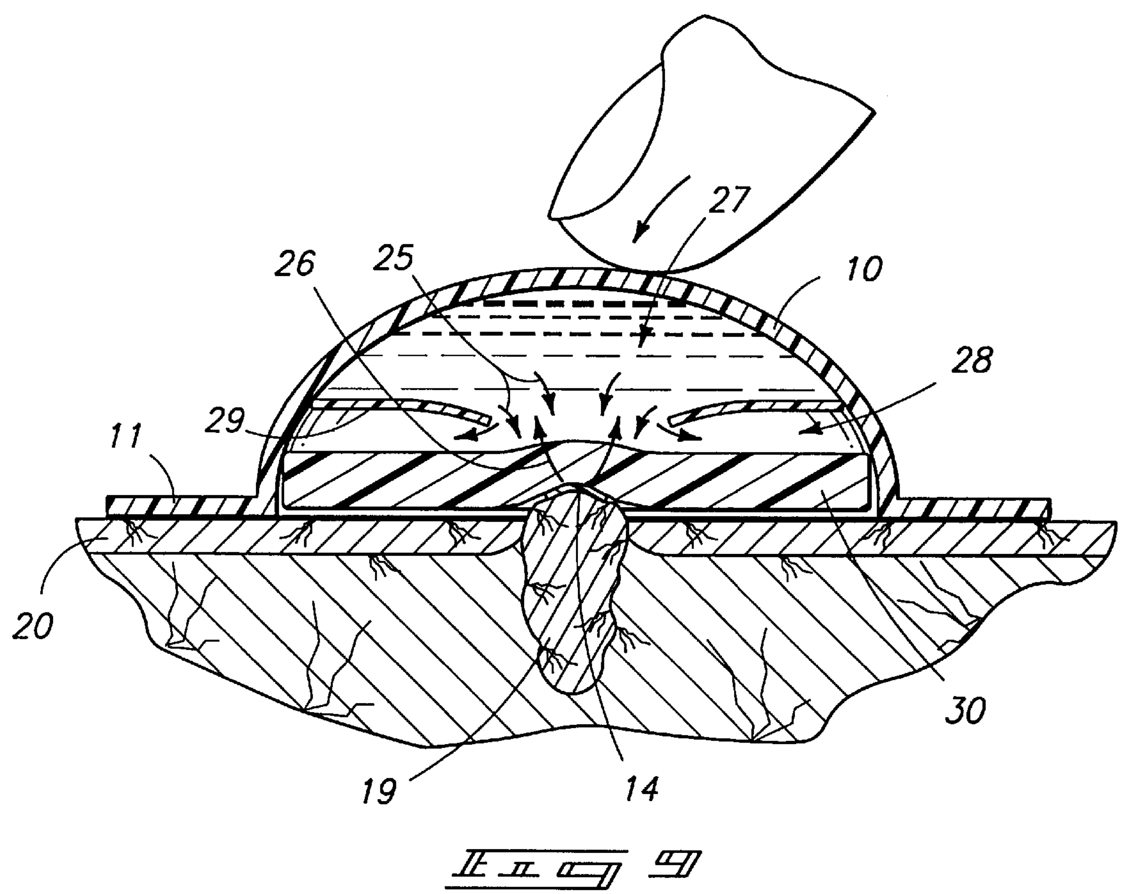
FIG. 9 is a view illustrating application of pressure and release of contactant.

The rupturable membrane 15 should readily separate or shatter when a predetermined amount of manual pressure is applied to the covering shroud 10. See FIG. 4. This membrane 15 could consist of a laminated series of concentric layers or a single planar sheet having a series of etched or partially slit concentric weakened lines. Alternately it could be a laminated membrane including numerous designed weakened seals 17 as shown in FIG. 5. The amount of force required to break the membrane 15 might range from 5 to 50 lbs at the apex of the shroud 10, the preferred amount being between 5 to 10 lbs. The rest of the components forming the skin patch should be designed to withstand a force 2 to 3 times the force needed to rupture the membrane 15.

A pressure sensitive concentrically laminated membrane 15 made of annular sections of polyethylene vinyl acetate lightly sealed to one another is schematically illustrated in FIG. 5. As an example, it might be designed to rupture in response to the application of 7 pounds of force to the shroud. It can be heat sealed to the shroud 10 about the periphery of the membrane 15. One or more saturated paper discs containing gentian violet are preferably adhered to the undersurface of the rupturable membrane 15.

The enclosed contactant delivery system might be completed by a release liner 16 that covers the exposed adhesive surface about flange 11 and the undersurface of the rupturable membrane 15.

The peel away release liner 16 can be composed of silicon rubber, cellophane, cellulose acetate, ethylcellulose, plasticized vinylacetate-vinylchloride copolymers, polyethylene terephthalate, nylon, polyethylene, polypropylene, polyvinylidenechloride, metal foils and sylanized polyester, paper, plastic or cellophane. The basic requirements of liner 16 is that it is impermeable to the contactant and solvent and readily removable to expose the adhesive about flange 11.

The use and application of the first embodiment of the device shall now be described for the treatment of warts.

First, the diagnosis is established by a health care provider. The proper size of the device can be determined by the size of the wart by physical examination. The peel-away release liner 16 is then removed to prepare the skin patch for application to the skin area to be treated. See FIG. 2.

The flexible skin patch is placed directly on the skin to cover the wart and a 2 to 3 mm area of surrounding normal skin. See FIG. 3. Adhesion to the skin is assured by the rim of pressure sensitive adhesive material along the undersurface of the flange 11 surrounding the skin patch.

Manual pressure is next applied to the shroud 10 by the index finger and/or thumb in sufficient force to break the rupturable membrane 15 at the base of the skin patch. This pressure will produce small cracks in the membrane 15 and permit passage of the solvent and contactant through it, as indicated by arrows 25 in FIG. 4.

The solvent and solubilized contactant will be released immediately from the containment chamber 12 during application of force to the shroud to promptly saturate the contacted skin. Over a period of time, additional contactant will be slowly released from the device and diffuse to the underlying skin surface.

The contactant (squaric acid dibutyl ester) will come into contact with the epidermis and pass into the dermis. At the same time, the indicator dye on discs 14 will diffuse back through the gel (as shown by arrows 26 in FIG. 4) until it becomes visible at the apex of the shroud 10.

As the molecules of squaric acid dibutyl ester come into contact with antigen presenting cells in the epidermis and dermis, an immune response will be mounted by the activated lymphocytes recruited to the area as part of the body's immune response. This will result in the viral particles being destroyed by cell mediated and antibody mediated mechanisms.

A rash will become apparent around the wart after 2 weeks from the first application. Subsequent applications of the device at two week intervals should be made until the wart resolves. The dosing schedule may vary depending upon the severity of the reaction seen and the response to treatment.

EXAMPLE 1

A single reservoir system for the delivery of squaric acid dibutyl ester to the skin has been experimentally constructed. It was formed as a polyethylene outer occlusive shroud enclosing a single chambered reservoir containing polyvinylpyrrolidone and butanol. A rupturable membrane formed as a layer of polyethylene was heat sealed across the formed shroud to serve as the bottom of the single liquid reservoir. A peel-away release liner temporarily enclosed the resulting skin patch.

The shroud of the skin patch was formed from a transparent is polyethylene sheet that was 5 mm thick and cut to 1 cm by 1 cm dimensions. A 3 mm diameter hemispheric bubble reservoir was formed in its center. The reservoir was formed under vacuum pressure applied to the sheet after briefly heating it with infra-red lights. After cooling, a polyacrylate adhesive was applied to the undersurface of the flange formed about the perimeter of the shroud.

88 mg of polyvinylpyrrolidone was mixed with 10 ml of butanol to produce a thick viscous solution. 2 mg of squaric acid dibutyl ester was then be added to 98 mg of the above solution and mixed with a mechanical blender to produce a 2% by weight concentration of the active contactant. A 5 ml volume of this solution was added to the reservoir system formed above.

A 3 mm paper disk was saturated with gential violet marking dye and allowed to dry. It was then adhered to the outer surface (undersurface) of the rupturable membrane by use of an epoxy resin adhesive.

The patch is designed to be applied directly to the exterior of a wart after removal of the peel-layer. Manual pressure applied to the top of the reservoir will then rupture the membrane and permit the contents of the liquid reservoir to be released to the wart and surrounding surface of the skin.

The skin patch should be left in place for 24 hours before removal by the patient. The area of application can then be washed to remove any excess material from the skin surface as marked by the gentian violet indicator. In two weeks an erythematous rash will be produced around the wart and another skin patch can be applied by a health care provider at a follow-up examination. This process is repeated until the wart is noted to resolve. The frequency of replacement of the patch can be tailored to the response of the individual patient. The object of therapy will be that a erythematous rash 2 to 3 mm around the wart is maintained throughout treatment until the wart has clinically disappeared.

SECOND EMBODIMENT

In this implementation, the therapeutic skin patch consists of a two chambered delivery system, as illustrated in FIGS. 6–9.

The overall enclosure of this skin patch is the same as described with respect to FIGS. 1–4. Similar reference numbers are used in the drawings to designate corresponding components of the contactant delivery system.

In this form of the device, there is a separate solvent containment chamber 27 and a contactant containment chamber 28. The outermost chamber 27 contains a solvent in sufficient quantity to saturate the gel matrix 28 within the contactant chamber 28. The solvent is released upon the rupture of a membrane 29 forming the floor of the solvent containment chamber 27. The chamber 27 might also contain a preservative or gelling agent.

The indicator dye is stored in a small area on the skin contact side of the gel matrix. Paper discs 14 containing the dye, as previously described, are preferably used for this purpose. The indicator dye will diffuse back through the gel matrix 30 in the contactant containment chamber 28 upon contact with the solvent. The dye will also diffuse onto the skin 20 with the released contactant and will be visible through the transparent apex of the shroud 10. This provides visible affirmation that the device has been activated on the skin.

As previously described, the gel matrix 30 can be made to contain varying concentrations of contactants from 0.001% to 30% by volume, but preferably contains a 2% concentration of contactant by volume. The contactant, such as squaric acid dibutyl ester, is interspersed evenly throughout the gel. Upon contact with solvent, the gel matrix 30 releases contactant to the surface of skin 20 surrounding a wart 19.

The rupturable membrane 29 between the contactant containment chamber 28 and the solvent containment chamber 27 must tear or shatter when a predetermined amount of pressure is applied to the shroud 10. This membrane 29 also can consist of a laminated series of partial sheets that will separate in response to activating pressure, or can consist of a single planar sheet with etched or partially slit areas across its surfaces. Alternately it could be a membrane containing numerous weakened seals about it.

The amount of pressure used to break the seal provided by the membrane 29 might require from 5 to 50 lbs of force for activation of the skin patch. The preferred activation force is in the range of 5 to 10 lbs. The rest of the delivery device components would be designed to withstand a force 2 to 3 times the force needed to rupture the membrane.

The steps involved in using the two reservoir system shown in FIGS. 6–9 are essentially similar to those described with respect to the single reservoir system in FIGS. 1–5. When pressure is applied to the device to break the solvent containment chamber 27 (see FIG. 9), the solvent is released at the top of the device by mechanical forces transmitted to the rupturable membrane 29. This will produce small cracks in the membrane 29 that will be visible through shroud 10. These small cracks indicate that the device is active and allow passage of the solvent. Solvent will then flow into the gel matrix 30 to dissolve and release contactant.

The indicator dye within the discs 14 will slowly diffuse back through the gel matrix 30 until it becomes visible through shroud 10.

THIRD EMBODIMENT

A simplified delivery system may be effective in some applications where moisture or solvent in the form of water is already available, such as the bottom of a foot. See FIG. 10. This simplified system uses the endogenous perspiration present on the skin as the solvent for the previously-identified contactants. It can be used to treat warts on the plantar surface of the feet.

The device can simply consist of the outer shroud 10, a contactant in a gel matrix 35 and an adhesive-coated flange 11 covered by a release liner 16. Indicator dye can be provided within paper discs 14 secured to the underside of the gel matrix 35 by a suitable adhesive.

EXAMPLE 2

88 mg of carboxymethylcellulose powder were mixed with 10 ml of butanol to produce a thick semi-solid gel paste. 98 mg of this paste was then weighed and placed in a mechanical mixer. 2 mg of squaric acid dibutyl ester was mixed with the paste to produce a 2% concentration of contactant by weight. This paste was spread on a glass plate and compressed with a second glass plate with 2 mm spacers at the corners to produce a homogenous 2 mm thick film of carboxymethylcellulose/butanol/squaric acid dibutyl ester.

The glass plates were covered with a cellophane covering to facilitate removal of the resulting gel. The top glass plate covering the film was then removed and the gel was cut into 8 mm annular gel patches by use of a punch template.

A 3 mm paper disk was saturated with gential violet marking dye and allowed to dry. It was then implanted in the center of the gel on the side designed to contact the skin surface.

The 8 mm gel patch was applied to a 1 cm by 1 cm square piece of aluminum foil after first placing a small drop of epoxy resin at its center to secure the gel patch. The aluminum foil was subsequently applied to a 2 cm by 2 cm square piece of cloth woven bandage material having an undersurface that was coated with a polyacrylate adhesive. A 2 cm by 2 cm piece of peel-away layer of wax paper was applied to the undersurface of the bandage to complete assembly of the skin patch. Finally, the entire device should be sealed in a air tight aluminum foil pouch for storage.

Figure 10:
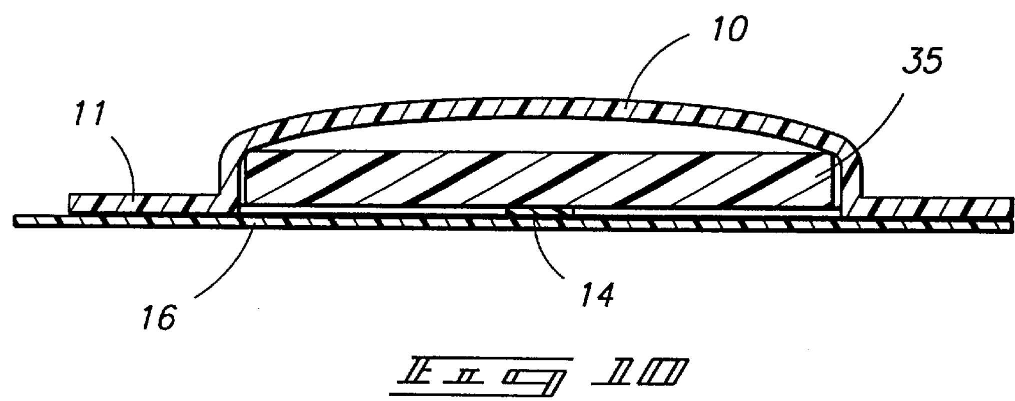
FIG. 10 is a schematic sectional view of a third embodiment of the skin patch.

The device shown in FIG. 10 can be applied to the plantar surface of a patient's foot in the following manner. The aluminum foil pouch must be opened and the peel-away backing removed. The patch can be applied directly to the wart against the skin surface. It should be left in place for 24 hours, after which it can be removed by the patient. The treated area is then washed to remove any excess material marked by the gentian violet dye visible on the skin surface. In two weeks an erythematous rash will be produced around the wart and a second skin patch should be reapplied by an attending health care provider at a follow-up examination.

The described treatment process should be repeated until the wart is noted to resolve. The frequency of replacement of the patch can be tailored to the response of the individual patient. The object of therapy being that a erythematous rash 2 to 3 mm around the wart is maintained throughout treatment until the wart has clinically disappeared.

FOURTH EMBODIMENT

FIG. 11 shows an additional structural feature within the skin patch, designed to enlarge the effective area of contactant application when using the device. In this modification, a flared shroud region is provided between the containment portion of the shroud 10 and the surrounding adhesive flange 11 to enlarge the area treated upon release of the contactant.

As in the first embodiment, the covering shroud 10 and a rupturable membrane 15 enclose a contactant containment chamber 12. A viscous solution of contactant and solvent substantially fill the chamber 12. One or more carrier discs 14 containing indicator dye are adhered to the underside of membrane 15 as previously described.

The device illustrated in FIG. 11 differs from those previously described in that it includes a peripheral flaring shroud region 40 leading radially outward from the periphery of the shroud 10. Shroud region 40 presents an open enclosed space of increased width adapted to be placed against the skin area under treatment. It is preferably formed integrally with the shroud 10 and made of the same flexible materials. Shroud region 40 leads to a surrounding flange 11 having an adhesive surface to which an enlarged release liner 16 is adhered to complete the contactant delivery system.

When applied about a wart (not shown), the apex of the shroud 10 can be manually depressed to rupture membrane 15 and release the solution of contactant and solvent. This fluid will pass through the membrane 15 and spread across the skin within the confines of the enlarged shroud region 40. In this manner, the volume of contactant within the patch can be minimized, while assuring application of it about a substantial area surrounding a wart or other skin condition under treatment. As the patch is activated, the dye provided on membrane 15 will become visible through the shroud 10 and will also be applied to the treated skin area. In all other respects, the formulation and usage of this embodiment of the skin patch is identical to those previously described.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A skin patch for the topical administration of controlled quantities of a contactant to intentionally induce a contact dermatitis for treatment of a medical condition responsive to contact immunotherapy, the patch comprising:

a standardized dosage of a contactant intended to induce a contact dermatitis in human skin, said contactant selected from the group comprised of dinitrochlorobenzene, squaric acid dibutyl ester, diphenlcyclopropenone, and their derivatives;

a shroud partially enclosing the contactant;

adhesive means associated with the shroud for temporarily and releasably attaching it to the skin of a user for a period of time sufficient to induce contact dermatitis; and a discardable release liner bonded to the adhesive means.

2. The skin patch of claim 1, wherein the contactant is provided within a viscous liquid solution.

3. The skin patch of claim 1, wherein the contactant is provided within a gel matrix.

4. The skin patch of claim 1, wherein the skin patch includes a single containment chamber containing the contactant.

5. The skin patch of claim 1, wherein the skin patch includes a single containment chamber containing both the contactant and a solvent.

6. A skin patch for the topical administration of controlled quantities of a contactant to intentionally induce a contact dermatitis for treatment of a medical condition responsive to contact immunotherapy, the patch comprising;

a gel matrix containing a standardized dosage of a contactant intended to induce a contact dermatitis in human skin, said contactant selected from the group comprised of dinitrochlorobenzene, squaric acid dibutyl ester, diphenylcycloproenone and their derivatives;

a shroud overlying the gel matrix, the shroud being impermeable to passage of the contactant;

a flange surrounding the shroud, the flange having an inner adhesive surface for temporarily and releasably attaching it to the skin of a user for a period of time sufficient to induce contact dermatitis; and a discardable release liner bonded to the adhesive surface of the flange for temporarily covering the adhesive means prior to use.

7. The skin patch of claim 6, wherein the concentration of contactant within the gel matrix is between 0.001% to 30% by weight.

8. The skin patch of claim 6, wherein the gel matrix and contactant is directly exposed upon removal of the release liner, the contactant being releasable from the gel matrix in response to its hydration by contacted skin.

9. A method of treating medical conditions is a patient responsive to contact immunotherapy, comprising the steps of:

a. adhesively applying to a skin surface of the patient a skin patch containing an effective amount of a contactant known to induce contact dermatitis in said patient, said contactant selected from the group comprised of dinitrochlorobenzene, squaric acid dibutyl ester, diphenylcyclopropenone and their derivatives;

b. maintaining said patch on the skin of the patient for a predetermined period of time sufficient to intentionally induce contact dermatitis, and then removing said patch; and c. reapplying additional skin patches containing said contactant at a predetermined intervals to maintain said contact dermantitis until said medical condition is resolved.

10. The method of claim 9, further comprising dispersing said contactant in a polymer gel.

11. The method of claim 10, further comprising controlling the rate of release of the contactant from the polymer gel by interposing a membrane capable of limiting the rate of diffusion from the gel to the skin of the patient.

12. The method of claim 10, further comprising increasing the penetration of the contactant into the skin of the patient by occluding the area to be treated with the skin patch.

13. The method of claim 12, further comprising the step of providing an excess of solvent to the contactant when added to the polymer gel.

14. The method of claim 10, further comprising the step of including an indicator dye as an indicator that a desired dose of contactant has been delivered to the patient.

* * * * *